United States Patent [19]
Klofta et al.

[11] Patent Number: 5,830,487
[45] Date of Patent: Nov. 3, 1998

[54] ANTI-VIRAL, ANHYDROUS, AND MILD SKIN LOTIONS FOR APPLICATION TO TISSUE PAPER PRODUCTS

[75] Inventors: Thomas James Klofta, Cincinnati, Ohio; John Paul Erspamer, Bartlett, Tenn.; Ronald Wayne Berg, Fairfield, Ohio

[73] Assignee: The Procter & Gamble Company, Cincinnati, Ohio

[21] Appl. No.: 658,342

[22] Filed: Jun. 5, 1996

[51] Int. Cl.$^6$ ................. A61K 9/10; A61K 7/00; A01N 25/34
[52] U.S. Cl. ............. 424/402; 424/101; 424/404; 428/286; 428/290
[58] Field of Search ................ 424/401, 402, 424/404; 426/72; 428/286, 290; 514/828, 846, 873, 871

[56] References Cited

U.S. PATENT DOCUMENTS

| | | | |
|---|---|---|---|
| 3,814,096 | 6/1974 | Weiss et al. | 128/260 |
| 4,112,167 | 9/1978 | Dake et al. | 428/154 |
| 4,481,243 | 11/1984 | Allen | 428/154 |
| 4,513,051 | 4/1985 | Lavash | 428/212 |
| 4,764,418 | 8/1988 | Kuenn et al. | 428/284 |
| 4,824,689 | 4/1989 | Kuenn et al. | 427/2 |
| 4,828,912 | 5/1989 | Hossain et al. | 428/289 |
| 4,897,304 | 1/1990 | Hossain et al. | 428/289 |
| 4,943,350 | 7/1990 | Bogart et al. | 162/158 |
| 4,975,217 | 12/1990 | Brown-Skrobot et al. | 252/107 |
| 5,525,345 | 6/1996 | Warner et al. | 424/402 |
| 5,525,346 | 6/1996 | Hartung et al. | 424/402 |
| 5,525,645 | 6/1996 | Warner et al. | 424/402 |

*Primary Examiner*—Thurman K. Page
*Assistant Examiner*—Sharon Howard
*Attorney, Agent, or Firm*—Bart S. Hersko; Larry L. Huston; E. Kelly Linman

[57] ABSTRACT

A lotion composition for killing such viruses as rhinovirus and influenza in addition to imparting a soft, lubricious, lotion-like feel when applied to tissue paper in amounts as low as from about 2 to about 20% by weight, and tissue paper treated with such lotion compositions are disclosed. The anti-viral action of the lotion is due to the addition of an organic acid such as citric acid or a mixture of adipic acid, glutaric acid, and succinic acids. The solubilization of the organic acids within the lotion matrix and with the infected mucus is aided by the addition of such hydrophilic solvents as propylene glycol and polyethylene glycols. The lubricious lotions also contain a plastic or fluid emollient such as petrolatum, an immobilizing agent such as a fatty alcohol or fatty acid to immobilize the emollient on the surface of the tissue paper web and optionally a non-ionic surfactant to improve wettability when applied to toilet tissue. Because less lotion is required to impart the desired soft, lotion-like feel benefits, detrimental effects on the tensile strength and caliper of the lotioned paper are minimized or avoided. The anhydrous nature of the lotions also aids in the maintenance of such physical properties as tensile and caliper.

20 Claims, 2 Drawing Sheets

ANTI-VIRAL, ANHYDROUS, AND MILD SKIN LOTIONS FOR APPLICATION TO TISSUE PAPER PRODUCTS

This application claims the benefit of commonly assigned patent application Ser. No. 165,767 filed Dec. 13, 1993, abandoned upon filing commonly assigned application Ser. No. 398,727 filed Mar. 6, 1995, now U.S. Pat. No. 5,525,345 issued Jun. 11, 1996.

TECHNICAL FIELD

This application relates to anhydrous and anti-viral lotion compositions for imparting a soft, lubricious feel to tissue paper and having the ability to kill certain virus strains coming into contact with the lotioned paper. In addition, these anhydrous and anti-viral lotions are mild to the skin. Since no water is intentionally added to these lotions leads to advantages in maintaining such paper physical properties as tensile and caliper. This application further relates to tissue paper treated with such anhydrous and anti-viral lotion compositions.

BACKGROUND OF THE INVENTION

In the household, preventing the spread of germs related to the common cold is a difficult but yet desirable task. It is well documented that many hours of productive work are lost due to individuals becoming infected with the common cold or influenza. In addition, many dollars are spent annually on medicines to temper the ailments associated with the common cold and influenza. To prevent or slow the spread of germs within the household, sprays, liquids, and soaps exist for general germ disinfection. Sprays are typically used to clean in and around sinks, bath tubs, showers and toilets. Liquid hard surface cleaners with anti-bacterial action are now available for cleaning floors, countertops and other hard surfaces. In addition, a variety of anti-microbial soaps can be purchased for skin and body cleansing.

When one suffers from the common cold or flu, one's mucus is the source of a very high concentration of viruses. After the mucus is blown into a facial tissue, the virus within the mucus has the potential to infect other individuals coming into contact with it. Transfer of the mucus on the tissue will likely be through accidental or unintentional contact.

As an example of a possible transfer scenario, consider a cold sufferer who accidentally leaves a mucus infected facial tissue on a hard surface of some type. This hard surface might be a kitchen countertop, a bathroom vanity surface, or simply a piece of furniture. Another family member or colleague may accidentally come into contact with the infected mucus after picking up the tissue to throw it away. After coming into such contact with the mucus on the tissue, it is very possible for that individual to become infected with the viral condition (i.e., common cold, influenza).

Another transmission scenario is through the disposal of the facial tissues contaminated with the virus containing mucus. After a household waste basket becomes filled with trash containing a high concentration of infected tissues, it obviously needs to be disposed of in some manner. During this transfer of the household trash into another larger disposal unit, the individual transferring the trash has a high probability of coming into contact with the infected mucus. Once again, this individual is at a higher risk for contracting the virus.

Many other potential modes of virus transmission are possible after the facial tissue has become infected with the mucus. To reduce the probability of cold and influenza transmission, the tissue coated with the anti-viral and anhydrous lotion described herein will kill such viruses as rhinovirus and influenza. Killing these viruses within the tissue will likely reduce the transmission of such ailments as the common cold and flu. Kimberly-Clark's Avert facial tissue product of several years back contained effective germ killers, but the anionic surfactant in their germ killing vehicle was likely too irritating to the skin. As is well known, cold and flu sufferers typically have sore and irritated skin regions associated with the nose and lips. After blowing the aqueous mucus into the tissue, the anionic surfactant becomes easily dissolved and partially transferred to the irritated skin regions. These sensitive skin regions are more prone to irritation by anionic surfactants.

As noted, the irritation, inflammation and redness around the nose and lips can have several causes. A prime one is, of course, the sheer necessity of frequently blowing one's nose into the tissue, and wiping the resultant nasal discharge from the nose and surrounding area. The degree of irritation and inflammation caused by such blowing and wiping is directly proportional to: (1) the surface roughness of the tissue used; (2) the number of times the nose and its surrounding areas are in contact with the tissue; and (3) the irritation potential of any additives applied to the tissue paper. It is thus imperative to use ingredients within the anti-viral lotion that are as mild as possible. In fact, it is more desirable to use ingredients that might provide a skin benefit.

In addition to the adverse skin reactions in Avert, there was very little probability for dry transfer of their anti-viral formulations to the skin. This was partly due to the addition of the Avert anti-viral composition to a third ply of tissue which was then sandwiched between two outside plies. In addition, the Avert anti-viral composition was made up of crystalline solids. Thus, after pulling out a tissue from the dispensing box, the probability of transferring the anti-viral components to the fingers was low. Whereas, in the present invention, the anti-viral and anhydrous lotions can be readily transferred either to the skin or to inanimate objects by simply applying pressure between the lotioned tissue and the object being touched. Thus, the probability for skin or inanimate surface transfer is high, making it possible to kill viruses on animate and inanimate objects.

Accordingly, it would be desirable to provide lotioned tissue products that: (1) kills rhinovirus and influenza viruses within the tissue; (2) contains an anhydrous, anti-viral lotion that can be transferred to the skin or inanimate objects to kill viruses coming into contact with those lotioned skin or inanimate regions; (3) do not adversely affect the tensile strength, absorbency and caliper of the product; (4) are mild to the skin; (5) possess a soft and lubricious feel; (6) provide skin benefits associated with alpha hydroxy acids; (7) anhydrous lotion limits lotion diffusion and aids in the maintenance of such physical properties as tensile and caliper; (8) optionally contain a natural oil such as eucalyptol, menthol, thymol, camphor, lemon oil, methyl salicylate and mixtures thereof; and (9) do not require special wrapping or barrier materials for packaging.

SUMMARY OF THE INVENTION

The present invention relates to a substantially anhydrous lotion composition that is solid at ambient temperatures (i.e., at 20° C.) and imparts a soft, lubricious, lotion-like feel when applied to tissue paper. This lotion composition comprises:

(A) from about 1 to 25% of an anti-viral organic acid which is solid at room temperature and comprising a member selected from the group consisting of citric acid, adipic acid, glutaric acid, succinic acid, and mixtures thereof;

(B) from about 5 to about 25% of a substantially water free hydrophilic solvent having the ability to dissolve the anti-viral organic acid and comprising a member selected from polyethylene glycols ranging in molecular weight of from about 200 to about 900, propylene glycol, glycerin, hexylene glycol, and mixtures thereof;

(C) from about 5 to 60% of skin emollients having a plastic or fluid consistency at 20° C. and comprising a member selected from petroleum-based emollients, fatty acid ester emollients, fatty alcohol emollients, and mixtures thereof;

(D) from about 5 to about 50% of an agent capable of immobilizing the emollient and other ingredients on the surface of the tissue paper treated with the anti-viral lotion composition; the immobilizing agent having a melting point of at least about 35° C. and comprising a member selected from the group consisting of $C_{12}$–$C_{22}$ fatty alcohols, $C_{12}$–$C_{22}$ fatty acids, sorbitan stearates, waxes, and mixtures thereof;

(E) from about 1 to 50% of a substantially water free non-ionic surfactant having an HLB value of at least about 4 and which is mild to the skin, allows emulsification of the organic acid/solvent mixture into the hydrophobic emollient mixture, and allows for sufficient water absorbencies of the lotioned tissue; the non-ionic surfactants are preferably selected from ethoxylated fatty alcohol and ethoxylated sorbitan mono, di, and tri-alkyl derivatives and mixtures thereof; and (F) optionally from about 0.1% to about 20% of a natural oil, vitamin, or other additive comprising a member selected from the group consisting of aloe, vitamin E, panthenol, camphor, thymol, menthol, eucalyptol (cineole), geraniol, lemon oil, methyl salicylate, and clove, and mixtures thereof.

The present invention further relates to lotioned tissue papers wherein the lotion composition is applied to at least one surface thereof in an amount of from about 2 to about 30% by weight of the dried tissue paper. For example in the case of a 2-ply facial tissue product, the anti-viral lotion may be applied to each of the outside surfaces of the two plies. Alternatively, the lotion application equipment may be modified such that the anti-viral lotion is applied to the inside surface of each of the two plies. In addition, a third ply which has been coated on one or both sides with the anti-viral lotion can be inserted between the two coated or uncoated tissue plies. Other application permutations of the previous can also be used.

Lotioned tissue papers according to the present invention have a desirable, lubricious, lotion-like feel. Because anti-viral organic acids are added to the lotions, viruses such as rhinovirus and influenza can be killed within the tissue. Since the organic citric acid is of the alpha hydroxy acid type, some or all the skin benefits associated with these types of acids may be transferred to the user. In addition, other chemicals within the lotion can provide anti-microbial action. These chemicals include the glycol based solvents, natural oils, and the fatty alcohol emollients. The lotions are substantially anhydrous, enabling more efficient dry transfer of the lotion. Intentional addition of water to the lotion would be detrimental to such physical properties as tensiles and caliper. Water aids in the migration of the lotion throughout the tissue web. This leads to fiber debonding and less lotion concentrated at the surface of the paper. This leads to both tensile and caliper losses; thus, it is beneficial to maintain an anhydrous lotion state as described herein. In addition, water tends to promote microbial growth; thus, it is advantageous to maintain an anhydrous lotion state as described herein. Because the emollient is substantially immobilized on the surface of the tissue paper, less lotion composition is needed to impart the desired soft, lotion-like feel. As a result, the detrimental effects on the tensile strength and caliper of the tissue caused by prior mineral oil-containing lotions can be avoided. In addition, special barrier or wrapping materials are unnecessary in packaging the lotioned tissue products of the present invention.

DETAILED DESCRIPTION OF THE INVENTION

Figure 1:
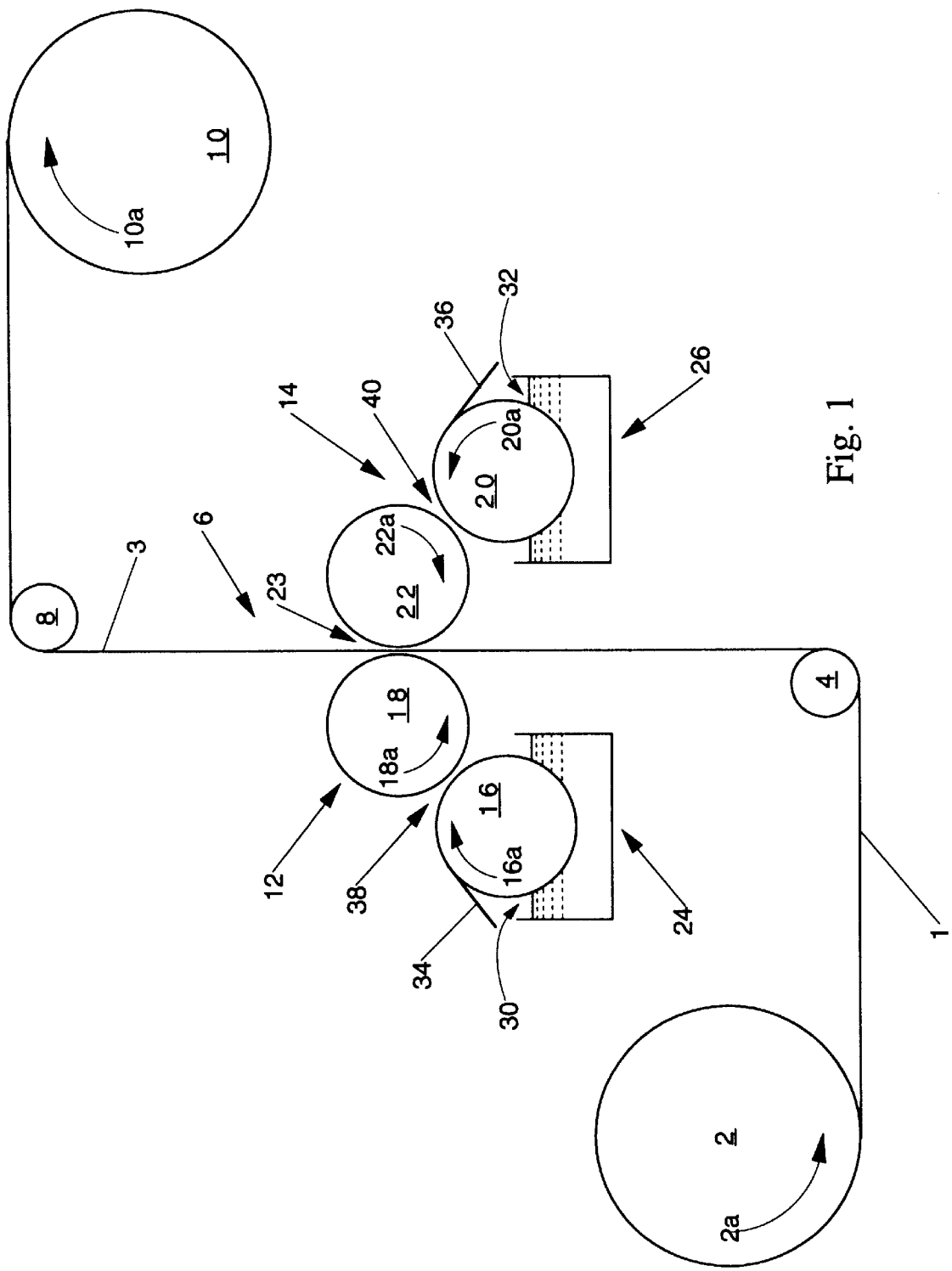
FIG. 1 is a schematic representation illustrating a preferred process for applying the lotion composition of the present invention to tissue paper webs.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

A. Tissue Papers

The present invention is useful with tissue paper in general, including but not limited to conventionally felt-pressed tissue paper; high bulk pattern densified tissue paper; and high bulk, uncompacted tissue paper. The tissue paper can be of a homogenous or multi-layered construction; and tissue paper products made therefrom can be of a single-ply or multi-ply construction. The tissue paper preferably has a basis weight of between about 10 g/m² and about 65 g/m², and density of about 0.6 g/cc or less. More preferably, the basis weight will be about 40 g/m² or less and the density will be about 0.3 g/cc or less. Most preferably, the density will be between about 0.04 g/cc and about 0.2 g/cc. See Column 13, lines 61–67, of U.S. Pat. No. 5,059,282 (Ampulski et al), issued Oct. 22, 1991, which describes how the density of tissue paper is measured. (Unless otherwise specified, all amounts and weights relative to the paper are on a dry basis.)

Conventionally pressed tissue paper and methods for making such paper are well known in the art. Such paper is typically made by depositing a papermaking furnish on a foraminous forming wire, often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided from a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The tissue paper structures that are formed are referred to hereafter as conventional, pressed, tissue paper structures. Such sheets are considered to be compacted since the entire web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non ornamental configuration or can be formed so as to provide an ornamental design(s) in the tissue paper. Preferred processes for making pattern densified tissue webs are disclosed in U.S. Pat. No. 3,301,746 (Sanford et al), issued Jan. 31, 1967; U.S. Pat. No. 3,974,025 (Ayers), issued Aug. 10, 1976; and U.S. Pat. No. 4,191,609 (Trokhan) issued Mar. 4, 1980; and U.S. Pat. No. 4,637,859 (Trokhan) issued Jan. 20, 1987; all of which are incorporated by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further densified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles that operate as the array of supports that facilitate the formation of the densified zones upon application of pressure. The pattern of knuckles constitutes the array of supports previously referred to. Suitable imprinting carrier fabrics are disclosed in U.S. Pat. No. 3,301,746 (Sanford et al), issued Jan. 31, 1967; U.S. Pat. No. 3,821,068 (Salvucci et al), issued May 21, 1974; U.S. Pat. No. 3,974,025 (Ayers), issued Aug. 10, 1976; U.S. Pat. No. 3,573,164 (Friedberg et al.), issued Mar. 30, 1971; U.S. Pat. No. 3,473,576 (Amneus), issued Oct. 21, 1969; U.S. Pat. No. 4,239,065 (Trokhan), issued Dec. 16, 1980; and U.S. Pat. No. 4,528,239 (Trokhan), issued Jul. 9, 1985, all of which are incorporated by reference.

Preferably, the furnish is first formed into a wet web on a foraminous forming carrier, such as a Fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally predried to a selected fiber consistency from about 40% to about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000 (Salvucci et al), issued May 21, 1974 and U.S. Pat. No. 4,208,459 (Becker et al), issued Jun. 17, 1980, both of which are incorporated by reference. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least about 80%, and creping the web. Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25–50%, transferring the web to a thermal dryer such as a Yankee and creping the web. Overall, water is removed from the web by vacuum, mechanical pressing and thermal means. The resulting structure is strong and generally of singular density, but very low in bulk, absorbency and softness.

The papermaking fibers utilized for the present invention will normally include fibers derived from wood pulp. Other cellulosic fibrous pulp fibers, such as cotton linters, bagasse, etc., can be utilized and are intended to be within the scope of this invention. Synthetic fibers, such as rayon, polyethylene and polypropylene fibers, can also be utilized in combination with natural cellulosic fibers. One exemplary polyethylene fiber that can be utilized is Pulpex®, available from Hercules, Inc. (Wilmington, Del.).

Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, are preferred since they impart a superior tactile sense of softness to tissue sheets made therefrom. Pulps derived from both deciduous trees (hereafter, also referred to as "hardwood") and coniferous trees (hereafter, also referred to as "softwood") can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as toilet paper, paper towels, facial tissues and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene® 557H.

Polyacrylamide resins have also been found to be of utility as wet strength resins. These resins are described in U.S. Pat. No. 3,556,932 (Coscia et al), issued Jan. 19, 1971, and U.S. Pat. No. 3,556,933 (Williams et al), issued Jan. 19, 1971, both of which are incorporated herein by reference. One commercial source of polyacrylamide resins is American Cyanamid Co. of Stamford, Conn., which markets one such resin under the mark Parez® 631 NC.

Still other water-soluble cationic resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit) and CoBond 1000 (manufactured by National Starch and Chemical Company) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the finished tissue paper product, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the tissue paper.

In general, suitable starch binders for the present invention are characterized by water solubility and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn", H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

B. Lotion Composition

The lotion compositions of the present invention are solid, or more often semisolid, at 20° C., i.e. at ambient temperatures. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components.

The solid or semisolid consistency of the lotions at room temperature are due to the addition of high melting components such as the anti-viral organic acids, fatty alcohols, waxes, and non-ionic ethoxylated surfactants. The high melting and higher molecular weight alkane fraction of the petrolatum can also contribute to raising the melting point of these anti-viral lotions. Because organic acids such as citric acid, adipic acid, glutaric acid, succinic acid and mixtures thereof are added to these lotions, viruses such as rhinovirus and influenza which come into contact with the lotion on the tissue are killed. Some of the anti-viral organic acids used in these lotions are from a class of acids termed alpha hydroxy acids. Thus, the skin benefits associated with these alpha hydroxy acids can be provided to the consumer. Other anti-microbials within the lotion can also aid in the lotion's ability to kill germs. These additional anti-microbials include propylene glycol, hexylene glycol, glycerin, fatty alcohols, and some of the natural oils.

By being solid or semisolid at ambient temperatures, these lotion compositions do not have a tendency to flow and migrate into the interior of the tissue web to which they are applied. This means less lotion composition is required for imparting softness and lotion-like feel benefits. It also means there is less chance for debonding of the tissue paper that can potentially lead to decreases in tensile strength.

When applied to tissue paper, the lotion compositions of the present invention impart a soft, lubricious, lotion like feel to the user of the paper. This particular feel has also been characterized as "silky", "slick", "smooth", etc. Such a lubricious, lotion-like feel is particularly beneficial for those having more sensitive skin due to chronic conditions such as skin dryness or hemorrhoids, or due to more transient conditions such as colds or allergies. Transfer of the lotion to the skin provides the potential for skin benefits for those lotions containing alpha hydroxy acids. In addition, lotion transfer to the skin can potentially protect those regions from virus infection.

The lotions of the present invention are substantially anhydrous. By substantially anhydrous is meant no water is intentionally added to these anti-viral lotions. Typically, the ingredients used in the present invention contain about 5% or less water, preferably about 1.0% or less water, more preferably about 0.5% or less water, and most preferably about 0.1% or less water. The anhydrous nature of these lotions allows for more efficient dry transfer of the lotion to the skin. Intentional addition of water to the lotion would be detrimental to such physical properties as tensiles and caliper. Water aids in the migration of the lotion throughout the tissue web. This leads to fiber debonding and less lotion concentrated at the surface of the paper. This leads to both tensile and caliper losses; thus, it is beneficial to maintain an anhydrous lotion state as described herein. Also, since the absence of water promotes greater surface concentration of the lotion ingredients, the probability for more efficient dry skin transfer is enhanced. In addition, water tends to promote microbial growth; thus, it is advantageous to maintain an anhydrous lotion state as described herein.

The lotion compositions of the present invention comprise: (1) an anti-viral organic acid(s); (2) a hydrophilic solvent(s); (3) an emollient(s); (4) an immobilizing agent(s); (5) a hydrophilic surfactant(s); and (6) other optional components such as natural oils, vitamins, or aloe.

1. Anti-Viral Organic Acid

The key active ingredient in these lotion compositions is one or more anti-viral organic acids. As used herein, an anti-viral organic acid is a material that is capable of killing such viruses as rhinovirus and influenza. Fruit acids such as citric acid are especially useful in deactivating/killing viruses. In addition to providing anti-viral activity, those acids which are within the alpha hydroxy class of acids can provide skin benefits associated with the use of alpha hydroxy acids. Citric acid is an alpha hydroxy acid. The dibasic acids of adipic, glutaric, succinic, and mixtures thereof, have also been found to be effective in deactivating the viruses of influenza and rhinovirus.

In addition to their anti-viral properties, the use of the solid organic acids can contribute to lotion hardening and thus aid in preventing lotion migration within the fibrous paper substrate. The high melting points of the acids can also allow the lotion to solidify more quickly at the surface of the paper. This allows for more efficient use of the lotion and the surface confinement contributes to more effective virus kill as well as improved lotion feel.

Citric acid and the dibasic acids of adipic, glutaric, succinic, and mixtures thereof are especially effective virus killers in these lotion compositions. Other potentially useful acids include malic acid, maleic acid, tartaric acid, salicylic acid and glycolic acid. Mixtures of many of these would also likely lead to anti-viral activity. Many theories exist as to how organic acids deactivate viruses such as rhinovirsus and influenza. One possible mechanism for virus deactivation is the donation of protons from the acid to the amide nitrogen of one or all of the various proteins within the virus structure. This protonation leads to a net positive charge within the protein structure. This leads to repulsion between the protonated amide moieties of the high molecular weight protein molecules. This leads to denaturing of some or all of the protein structures within the virus. This denaturing or unfolding of the protein structure deactivates the virus.

Another potential mechanism for deactivation by the organic acids is through hydrolysis of the proteins and other molecules within the virus structure. This acid catalyzed hydrolysis most likely occurs through cleavage of the amide functionalities of the proteins making up the complex virus structure. This hydrolysis and breakage of the bonds of the proteins of the virus structure deactivates the virus and renders it ineffective in attacking healthy cells within the body. For enveloped viruses like influenza where the structure is surrounded by a lipid shell, the acid may also cause deactivation through hydrolysis of this lipid layer.

2. Hydrophilic Solvent(s)

Another important component(s) of these lotions is the incorporation of hydrophilic solvents to aid in the solubilization of the anti-viral organic acids. These solvents may be glycol type solvents such as glycerin, propylene glycol, and hexylene glycol. In addition to allowing solubilization of the organic acids, some of glycol type solvents are also known to be anti-microbial in nature. Also, these glycol type solvents can provide an increase in the viscosity of the lotion and thus prevent unwanted migration of the lotion components within the fibrous paper network. But, their primary use in this particular application is to aid in the solubilization of the anti-viral organic acid.

Other solvents suitable for use in the lotion formulas of the present invention are of the polyethylene glycol type ranging in molecular weight from about 200 to about 900, more preferably from 300 to about 500. Polyethylene glycols are known humectants and thus can also provide moisturizing benefits to the skin.

3. Emollient

The other active ingredient(s) in these lotion compositions are one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. For the purposes of the present invention, these emollients have either a plastic or fluid consistency at 20° C., i.e., at ambient temperatures. This particular emollient consistency allows the lotion composition to impart a soft, lubricious, lotion-like feel.

The emollients useful in the present invention are also substantially free of water. By "substantially free of water" is meant that water is not intentionally added to the emollient. Addition of water to the emollient or the lotion is not necessary in preparing or using the lotion compositions of the present invention and could require an additional drying step. In fact, it is undesirable and unnecessary to add water to these anti-viral lotions. The addition of water could lead to potential microbial growth in the lotions. In addition, water would lower the melting point of the lotion and aid in the migration of other lotion components within the paper fiber substrate This would have a negative impact on the tensile and caliper properties of the lotioned paper. However, minor or trace quantities of water in the emollient that are picked up as a result of, for example, ambient humidity can be tolerated without adverse effect. Typically, the emollients used in the present invention contain about 5% or less water, preferably about 1.0% or less water, more preferably about 0.5% or less water, and most preferably about 0.1% or less water.

Emollients useful in the present invention can be petroleum-based, fatty acid ester type, fatty alcohol type, polyethylene glycols, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum is a particularly preferred emollient for lotion compositions of the present invention because of its exceptional skin moisturizing benefits.

Fatty alcohols are also particularly preferred due to their higher melt points, more crystalline structure and exceptional skin feel. The high melt points of the fatty alcohols raises the melt point of the lotion and thus aids in preventing migration of the lotion throughout the fiber network. The linear structure of the fatty alcohols gives the lotion crystalline attributes and should lead to faster crystallization/ solidification onto the paper substrate surface. Thus, during application to the paper surface, the lotion should set up and solidify faster on the surface of the paper substrate. The concentrates the lotion at the surface and gives the lotioned paper product a superior feel and also leads to a more efficient use of the organic acid anti-viral agents. The hydroxyl group in the fatty alcohol may also contribute to the lotion's anti-microbial action.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Besides petroleum-based emollients, fatty acid ester emollients, and fatty alcohol emollients, the emollients useful in the present invention can include minor amounts (e.g., up to about 10% of the total emollient) of other, conventional emollients. These other, conventional emollients include propylene glycol, glycerin, hexylene glycol, polyethylene glycols, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$–$C_{28}$ fatty acids; other fatty esters of polyhydroxy alcohols; lanolin and its derivatives; silicone polyether copolymers, and polysiloxanes having a viscosity at 20° C. of from about 5 to about 2,000 centistokes such as disclosed in U.S. Pat. No. 5,059,282 (Ampulski et al), issued Oct. 22, 1991, which is incorporated by reference. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 5 to about 60% of the emollient, more preferably from about 10 to about 40%.

4. Immobilizing Agent

An especially key component of the lotion compositions of the present invention is an agent capable of immobilizing the emollient on the surface of the paper to which the lotion composition is applied. Because some of the emollients in the composition have a plastic or fluid consistency at 20° C., it tends to flow or migrate, even when subjected to modest shear. When applied to a tissue paper web, especially in a melted or molten state, the emollient will not remain primarily on the surface of the paper. Instead, the emollient will tend to migrate and flow into the interior of the paper web.

This migration of the emollient into the interior of the web can cause undesired debonding of the paper by interfering with the normal hydrogen bonding that takes place between the paper fibers. This usually leads to a decrease in tensile strength of the paper. It also means much more emollient has to be applied to the paper web to get the desired lubricious, lotion-like feel benefits. Increasing the level of emollient not only increases the cost, but also exacerbates the debonding problem of the paper. The caliper can also be negatively impacted if no immobilizing agent is used. With no immobilizer, the lotion migrates throughout the fiber web instead of concentrating itself at the paper's surface. In severe cases where liquid emollients are employed, the caliper can actually decrease.

The immobilizing agent counteracts this tendency of the emollient to migrate or flow by keeping the emollient primarily localized on the surface of the tissue paper web to which the lotion composition is applied. This is believed to be due, in part, to the fact that the immobilizing agent forms hydrogen bonds with the tissue paper web. Through this hydrogen bonding, the immobilizing agent becomes localized on the surface of the paper. Since the immobilizing agent is also miscible with the emollient (or solubilized in the emollient with the aid of an appropriate emulsifier), it entraps the emollient on the surface of the paper as well. Immobilization is also enhanced by a more crystalline structure of the immobilizing agent. If the immobilizing agent is more crystalline in structure, the immobilization molecules will tend to quickly form seeds of nucleation sites where the lotion can solidify. The more amorphous immobilization agents tend to solidify at much slower rates than their more crystalline counterparts.

It is also advantageous to "lock" the immobilizing agent on the surface of the paper This can be accomplished by using immobilizing agents which quickly crystallize (i.e., solidify) at the surface of the paper. In addition, outside cooling of the treated paper via blowers, fans, etc. can speed up crystallization of the immobilizing agent.

In addition to being miscible with (or solubilized in) the emollient, the immobilizing agent needs to have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

The viscosity of the immobilizing agent should also be as high as possible to keep the lotion from flowing into the interior of the paper. Unfortunately, high viscosities can also lead to lotion compositions that are difficult to apply without processing problems. Therefore, a balance must be achieved so the viscosities are high enough to keep the immobilizing agent localized on the surface of the paper, but not so high as to cause processing problems. Suitable viscosities for the immobilizing agent will typically range from about 5 to about 200 centipoises, preferably from about 15 to about 100 centipoises, measured at 60° C.

Suitable immobilizing agents for the present invention can comprise a member selected from the group consisting of $C_{14}$–$C_{22}$ fatty alcohols, $C_{12}$–$C_{22}$ fatty acids, sorbitan stearates, waxes, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of cetyl acid, stearyl acid, and mixtures thereof. Mixtures of cetyl acid and stearyl acid are particularly preferred. Still other preferred immobilizing agents include paraffin type waxes, sorbitan stearates, and mixtures thereof. Preferably, the fatty alcohols and fatty acids are linear.

Importantly, these preferred immobilizing agents such as the $C_{16}$–$C_{18}$ fatty alcohols increase the rate of crystallization of the lotion causing the lotion to crystallize rapidly onto the surface of the substrate. Lower lotion levels can therefore be utilized so a superior lotion feel can be delivered. Traditionally, greater amounts of lotion were needed to generate softness because of the flow of these liquids into the bulk paper substrate.

Other types of immobilizing agents can be used in combination or in place of the fatty alcohols, fatty acids, sorbitan stearates and waxes described above. Typically, only minor amounts of these other types of immobilizing agents would be used (i.e., up to about 10% of the total immobilizing agent). However, using larger amounts of these other types of these immobilizing agents (i.e., up to 100%) is within the scope of the present invention. Examples of these other types of immobilizing agents includes polyhydroxy fatty acid esters, polyhydroxy fatty acid amides, and mixtures thereof. To be useful as immobilizing agents, the polyhydroxy moiety of the ester or amide should have at least one free hydroxy group. It is believed that these free hydroxy group(s) are the ones that co-crosslink through hydrogen bonds with the cellulosic fibers of the tissue paper web to which the lotion composition is applied and homo-crosslink, also through hydrogen bonds, the hydroxy groups of the alcohol, acid, ester or amide, thus entrapping and immobilizing the other components in the lotion matrix.

It is also believed that molecules such as long chain fatty alcohols can orient themselves and interact with one another to form a lamellar structure. In this lamellar structure, the hydroxyl groups and alkyl chains of neighboring alcohol molecules orient and interact with one another to form an organized structure. In this "packing arrangement," the hydroxyl groups of the alcohols form hydrogen bonds with the cellulose polar functionalities (e.g., hydroxy or carbonyl) to "immobilize" the alcohols at the paper's surface. Since the alcohols are miscible with the preferred emollients, anchoring and/or immobilization of the emollient will occur.

Preferred esters and amides will have three or more free hydroxy groups on the polyhydroxy moiety and are typically nonionic in character. Because of the possible skin sensitivity of those using paper products to which the lotion composition is applied, these esters and amides should also be relatively mild and non-irritating to the skin.

Suitable polyhydroxy fatty acid esters for use in the present invention will have the formula:

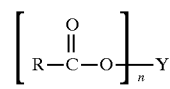

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters are particularly preferred and include sucrose monostearate and sucrose monolaurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2(CHOH)_n$—$CH_2OH$, —$CH(CH_2OH)$—$[(CHOH)_{n-1}]$—$CH_2OH$, —$CH_2OH$—$CH_2$—$(CHOH)_2$ $(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl, $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

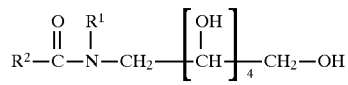

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}$ $(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of steareth-2 and sorbitan tristearate as the emulsifier.

The amount of immobilizing agent that should be included in the lotion composition will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 80% of the immobilizing agent. Preferably, the lotion composition comprises from about 5 to about 50%, most preferably from about 10 to about 30%, of the immobilizing agent.

5. Hydrophilic Surfactant

In many instances, lotion compositions according to the present invention will be applied to tissue paper webs that will be used as toilet tissue. In such cases, it is highly desirable that the paper web treated with the lotion composition be sufficiently wettable. Depending upon the particular immobilizing agent used in the lotion composition of the present invention, an additional hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 will require addition of hydrophilic surfactant to improve wettability if the lotion composition is applied to paper webs used as toilet tissue. Similarly, a hydrophobic emollient such as petrolatum will require the addition of a hydrophilic surfactant.

Suitable hydrophilic surfactants will be miscible with the emollient and the immobilizing agent so as to form homogeneous mixtures. Because of possible skin sensitivity of those using paper products to which the lotion composition is applied, these surfactants should also be relatively mild and non-irritating to the skin. Typically, these hydrophilic surfactants are nonionic to be not only non-irritating to the skin, but also to avoid other undesirable effects on the tissue paper, e.g., reductions in tensile strength.

Suitable nonionic surfactants will be substantially non-migratory after the lotion composition is applied to the tissue paper web and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of tissue paper products, e.g., at least about 30° C. In this regard, these nonionic surfactants will preferably have melting points similar to those of the immobilizing agents previously described.

Suitable nonionic surfactants for use in lotion compositions of the present invention include alkylglycosides; alkylglycoside ethers as described in U.S. Pat. No. 4,011,389 (Langdon, et al), issued Mar. 8, 1977; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 76 (i.e., Steareth-10) and Brij 56 (i.e., Cetyl-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to increase the wettability of the lotion composition to a desired level will depend upon the HLB value and level of immobilizing agent used, the HLB value of the surfactant used and like factors. The lotion composition can comprise from about 1 to about 50% of the hydrophilic surfactant when needed to increase the wettability properties of the composition. Preferably, the lotion composition comprises from about 5 to about 25% of the non-ionic surfactant.

Since maintaining skin mildness is an important factor in the production of lotioned tissue products, the use of non-ionic surfactants is preferred since they are milder to the skin than charged surfactants. This is not to state that all charged surfactants are irritating to the skin. But, as a general rule, most charged surfactants are irritating to the skin. The non-ionic surfactants used in these anti-viral lotions serve several important functions. One critical function is to allow the hydrophilic acid/solvent mixture to mix with the hydrophobic emollients. This allows for a stable blend of the hydrophobic components to be made with the hydrophilic components.

In addition to providing lotion stability, the surfactant also allows the lotioned paper to absorb water and mucus at a reasonable rate. If no surfactant was formulated into the lotion, the lotioned paper product would in some cases repel water and mucus and cause negative consumer reactions.

It is important for the lotioned tissue paper according to the present invention to be absorbent and/or wettable, as reflected by its hydrophilicity. Hydrophilicity of tissue paper refers, in general, to the propensity of the tissue paper to be wetted with water. Hydrophilicity of tissue paper can be quantified somewhat by determining the period of time required for dry tissue paper to become completely wetted with water. This period of time is referred to as the "wetting" (or "sinking") time. In order to provide a consistent and repeatable test for wetting time, the following procedure can be used for wetting time determinations: first, a paper sample (the environmental conditions for testing of paper samples are 23°±1° C. and 50 ±2% RH. as specified in TAPPI Method T 402), approximately 2.5 inch×3.0 inches (about 6.4 cm×7.6 cm) is cut from an 8 sheet thick stack of conditioned paper sheets; second, the cut 8 sheet thick paper sample is placed on the surface of 2500 ml. of distilled water at 23°±1° C. and a timer is simultaneously started as the bottom sheet of the sample touches the water; third, the timer is stopped and read when wetting of the paper sample is completed, i.e. when the top sheet of the sample becomes completely wetted. Complete wetting is observed visually.

The preferred hydrophilicity of tissue paper depends upon its intended end use. It is desirable for tissue paper used in a variety of applications, e.g., toilet paper, to completely wet in a relatively short period of time to prevent clogging once the toilet is flushed. Typically, wetting time is 4 minutes or less, preferably, wetting time is 90 seconds or less, more preferably 30 seconds or less, and most preferably, wetting time is 10 seconds or less.

The hydrophilicity of tissue paper can, of course, be determined immediately after manufacture. However, substantial increases in hydrophobicity can occur during the first two weeks after the tissue paper is made: i.e. after the paper has aged two (2) weeks following its manufacture. Thus, the above stated wetting times are preferably measured at the end of such two week period. Accordingly, wetting times measured at the end of a two week aging period at room temperature are referred to as "two week wetting times."

The higher melting non-ionic surfactants can also contribute to hardening of the lotion and thus aid in confining the lotion at the surface of the paper substrate. Importantly in relation to anti-viral activity, the surfactant can function to aid in solubilizing the lipid shell layer of the enveloped class of viruses. This solubilization of the lipid shell enhances the ability of the anti-viral acids to penetrate into the virus structure and deactivate it.

6. Other Optional Components

Lotion compositions can comprise other optional components typically present in emollients, creams, and lotions of this type. These optional components include water, viscosity modifiers, perfumes, disinfectant and other antibacterial actives, pharmaceutical actives, film formers, vitamins (e.g. vitamin E), deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed in appropriate amounts in the lotion compositions of the present invention. In addition, natural oils such as camphor, thymol, menthol, eucalyptol (cineole), geraniol, lemon oil, methyl salicylate, clove and other similar materials may be used to give the product a medicinal scent. In addition, many of these natural oils also possess anti-viral properties.

C. Treating Tissue Paper With Lotion Composition

In preparing lotioned paper products according to the present invention, the lotion composition is applied to at least one surface of a tissue paper web. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the surface of the paper web. The lotion composition can be applied either to one surface of the tissue paper web, or both surfaces. Preferably, the lotion composition is applied to both surfaces of the paper web.

The manner of applying the lotion composition to the tissue paper web should be such that the web does not become saturated with the lotion composition. If the web becomes saturated with the lotion composition, there is a greater potential for debonding of the paper to occur, thus leading to a decrease in the tensile strength of the paper. Also, saturation of the paper web is not required to obtain the softness and lotion-like feel benefits from the lotion composition of the present invention. Particularly suitable application methods will apply the lotion composition primarily to the surface, or surfaces of the paper web.

The lotion composition can be applied to the tissue paper web after the web has been dried, i.e. a "dry web" addition method. The lotion composition is applied in an amount of from about 2 to about 30% by weight of the tissue paper web. Preferably, the lotion composition is applied in an amount of from about 5 to about 20% by weight of the tissue paper web, most preferably from about 10 to about 16% by weight of the web. Such relatively low levels of lotion composition are adequate to impart the desired softness and lotion-like feel benefits to the tissue paper, yet do not saturate the tissue paper web to such an extent that absorbency, wettability and particularly, strength, are substantially affected.

The lotion composition can also be applied non uniformly to the surface(s) of the tissue paper web. By "non uniform" is meant that the amount, pattern of distribution, etc. of the lotion composition can vary over the surface of the paper. For example, some portions of the surface of the tissue paper web can have greater or lesser amounts of lotion composition, including portions of the surface that do not have any lotion composition on it.

The lotion composition can be applied to the tissue paper web at any point after it has been dried. For example, the lotion composition can be applied to the tissue paper web after it has been creped from a Yankee dryer, but prior to calendering, i.e., before being passed through calender rolls. The lotion composition can also be applied to the paper web after it has passed through such calender rolls and prior to being wound up on a parent roll. Usually, it is preferred to apply the lotion composition to the tissue paper as it is being unwound from a parent roll and prior to being wound up on smaller, finished paper product rolls.

The lotion composition is typically applied from a melt thereof to the tissue paper web. Since the lotion composition melts at significantly above ambient temperatures, it is usually applied as a heated coating to the tissue paper web. Typically, the lotion composition is heated to a temperature in the range from about 35° to about 100° C., preferably from 40° to about 90° C., prior to being applied to the tissue paper web. Once the melted lotion composition has been applied to the tissue paper web, it is allowed to cool and solidify to form solidified coating or film on the surface of the paper.

In applying lotion compositions of the present invention to tissue paper webs, gravure coating and extrusion coating methods are preferred. FIG. 1 illustrates one such preferred method involving gravure coating. Referring to FIG. 1, a dried tissue web 1 is unwound from parent tissue roll 2 (rotating in the direction indicated by arrow 2a) and advanced around turning roll 4. From turning roll 4, web 1 is advanced to offset-gravure coating station 6 where the lotion composition is then applied to both sides of the web. After leaving station 6, web 1 becomes a lotioned web indicated by 3. Lotioned web 3 is then advanced around turning roll 8 and then wound up on lotioned tissue parent roll 10 (rotating in the direction indicated by arrow 10a).

Station 6 comprises a pair of linked offset-gravure presses 12 and 14. Press 12 consists of a lower gravure cylinder 16 and an upper offset cylinder 18; press 14 similarly consists of a lower gravure cylinder 20 and an upper offset cylinder 22. Gravure cylinders 16 and 20 each have a specific etched cell pattern and size, and each have a chrome plated surface, while offset cylinders 18 and 22 each have a smooth polyurethane rubber surface. The size of the cell volume of the gravure roll will depend upon the desired coat weight, line speed, and lotion viscosity. Both the gravure and offset cylinders are heated to keep the lotion molten. These gravure and offset cylinders rotate in the directions indicated by arrows 16a, 18a, 20a and 22a, respectively. As shown in FIG. 1, offset cylinders 18 and 22 are directly opposite and parallel to each other and provide a nip area indicated by 23 through which web 1 passes.

Positioned beneath gravure cylinders 16 and 20 are fountain trays 24 and 26, respectively. Hot, molten (e.g., 65° C.) lotion composition is pumped into each of these heated trays 24 and 26 to provide reservoirs of the molten lotion composition, as indicated arrows by 30 and 32, respectively. As gravure cylinders 16 and 20 rotate in the directions indicated by arrows 16a and 20a within reservoirs 30 and 32, they pick up a quantity of molten lotion composition. Excess lotion on each of the gravure cylinders 16 and 20 is then removed by doctor blades 34 and 36, respectively.

The lotion composition remaining in the heated gravure cylinder cells 16 and 20 is then transferred to heated offset cylinders 18 and 22 (rotating in the opposite direction as indicated by arrows 18a and 22b) in nip areas 38 and 40 between the respective pairs of cylinders. The lotion composition transferred to offset cylinders 18 and 22 is then simultaneously transferred to both sides of web 1. The amount of lotion composition transferred to web 1 can be controlled by: (1) adjusting the width of nip area 23 between offset cylinders 18 and 22; and/or (2) adjusting the width of nip areas 38 and 40 between gravure/offset cylinder pairs 16/18 and 20/22.

Figure 2:
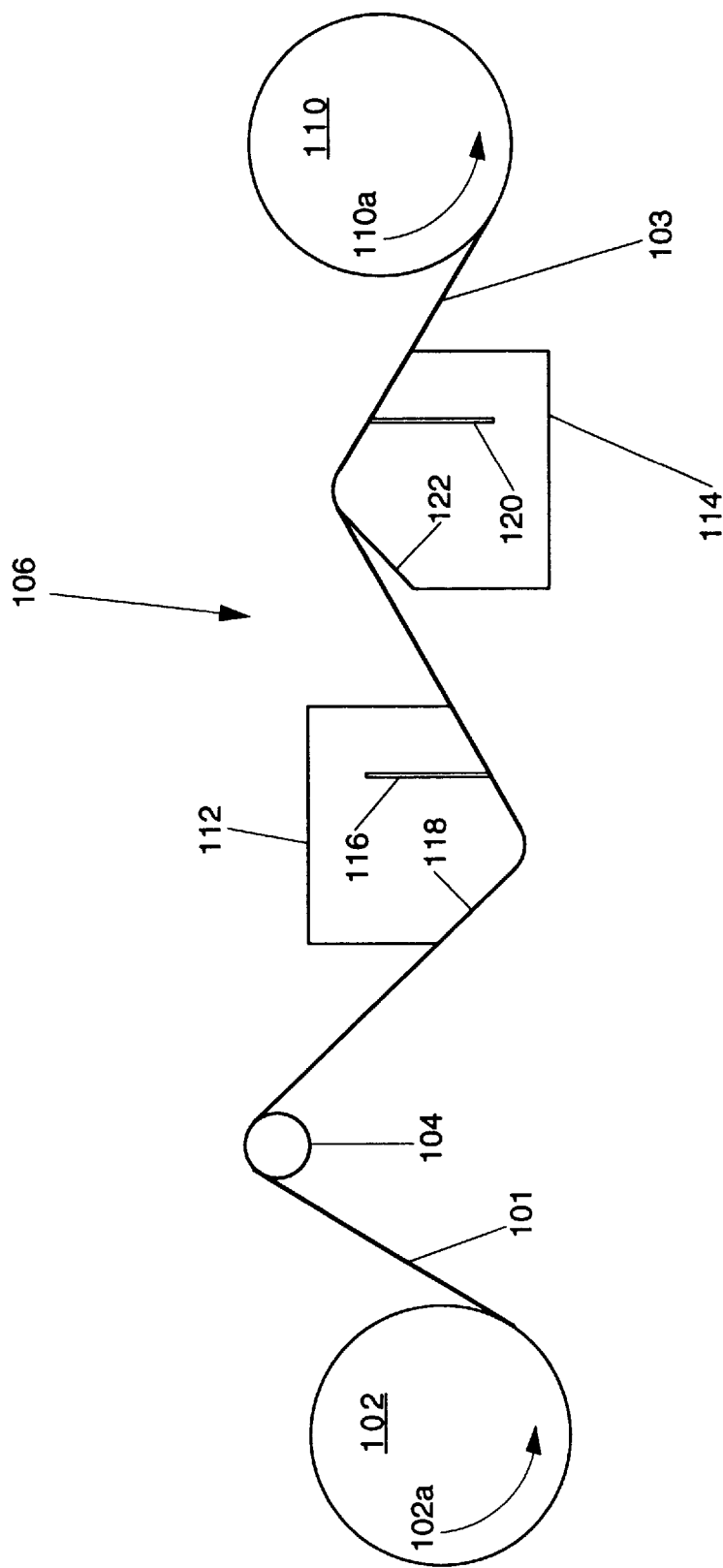
FIG. 2 is a schematic representation illustrating an alternative process for applying the lotion composition of the present invention to tissue paper webs.

FIG. 2 illustrates an alternative preferred method involving slot extrusion coating. Referring to FIG. 2, a dried tissue web 101 is unwound from parent tissue roll 102 (rotating in the direction indicated by arrow 102a) and then advanced around turning roll 104. From turning roll 104, web 101 is advanced to slot extrusion coating station 106 where the lotion composition is then applied to both sides of the web. After leaving station 106, web 101 becomes a lotioned web indicated by 103. Lotioned web 103 is then wound up on lotioned tissue parent roll 110 (rotating in the direction indicated by arrow 110a).

Station 106 comprises a pair of spaced slot extruders 112 and 114. Extruder 112 has an elongated slot 116 and a web contacting surface 118; extruder 114 similarly has an elongated slot 120 and a web contacting surface 122. As shown in FIG. 2, extruders 112 and 114 are oriented such that surface 118 is in contact with one side of web 101, while surface 122 is in contact with the other side of web 101. Hot, molten (e.g., 65° C.) lotion composition is pumped to each of extruders 112 and 114 and is then extruded through slots 116 and 120, respectively.

As web 101 passes over the heated surface 118 of extruder 112 and reaches slot 116, the molten lotion composition extruded from slot 116 is applied to the side of web 101 in contact with surface 118. Similarly, as web 101 passes over heated surface 122 of extruder 114 and reaches slot 120, the molten lotion composition extruded from slot 120 is applied to the side of web 101 in contact with surface 122. The amount of lotion composition transferred to web 101 is controlled by: (1) the rate at which the molten lotion composition is extruded from slots 116 and 122; and/or (2) the speed at which web 101 travels while in contact with surfaces 118 and 122.

SPECIFIC ILLUSTRATIONS OF THE PREPARATION OF LOTIONED TISSUE PAPER ACCORDING TO THE PRESENT INVENTION

The following are specific illustrations of treating tissue paper with lotion compositions in accordance with the present invention:

EXAMPLE 1

A. Preparation of Lotion Composition A

The water free Lotion Composition A is made by first mixing the following components together: propylene glycol, ceteareth-10, and citric acid. This mixture is heated to 60° to 90° C. and mixed until the citric acid has dissolved. After the citric acid has dissolved, fatty alcohols consisting predominately of a blend of cetyl and stearyl alcohols is added and mixed at a temperature of 60° to 90° C. After these fatty alcohols have dissolved, petrolatum is added and mixed at a temperature of 60° to 90° C. The petrolatum is mixed until the entire composition is phase stable and transparent. The weight percentages of these components are shown in Table I below:

TABLE I

| Lotion Composition A | |
|---|---|
| Component | Weight % |
| Citric Acid | 20.1 |
| Propylene Glycol | 10.1 |
| Ceteareth-10 | 10.0 |
| Cetearyl Alcohol | 25.2 |
| Petrolatum | 34.6 |

B. Preparation of Lotioned Tissue by Hot Melt Spraying

Lotion A is placed into a PAM 600S Spraymatic hot melt spray gun (made by PAM Fastening Technology, Inc.) operating at a temperature of ~90° C. Twelve inch by 12 inch sheets of tissue paper substrate are spray coated to the desired lotion level on each side of the substrate. The lotioned tissues are then placed in a 70° C. convection oven for 30 seconds after each side are sprayed to remove volatile components, and to insure a more even coating of the lotion onto the paper fibers.

EXAMPLE 2

A. Preparation of Lotion Composition B

The water free Lotion Composition B is made by first mixing the following components together: propylene glycol, polyethylene glycol 300 (PEG-300), ceteareth-10, and a mixture of adipic acid, glutaric acid, and succinic acids (AGS Acids). This mixture is heated to 60° to 90° C. and mixed until the adipic acid, glutaric acid and succinic acid have all dissolved. After the acids have dissolved, fatty alcohols consisting predominately of a blend of cetyl and stearyl alcohols are added and mixed at a temperature of 60° to 90° C. After these fatty alcohols have dissolved, petrolatum is added and mixed at a temperature of 60° to 90° C. The petrolatum is mixed until the entire composition is phase stable and transparent. The weight percentages of these components are shown in Table II below:

TABLE II

| Lotion Composition B | |
|---|---|
| Component | Weight % |
| Propylene Glycol | 5.0 |
| PEG-300 | 10.0 |
| Ceteareth-10 | 20.0 |
| AGS Acids | 15.0 |
| Cetearyl Alcohol | 25.0 |
| Petrolatum | 25.0 |

B. Preparation of Lotioned Tissue by Hot Melt Spraying

Melted Lotion B is placed into a PAM 600S Spraymatic hot melt spray gun operating at a temperature of 90° C. A 12 inch by 12 inch sheet of tissue paper substrate is spray coated to the desired lotion level on each side of the substrate. The lotioned tissue is placed in a 70° C. convection oven for 30 seconds after each side is sprayed to remove volatile components, and to insure a more even coating of the lotion onto the paper fibers.

What is claimed is:

1. A lotioned tissue paper having applied to at least one surface thereof, in an amount of from about 2 to about 30% by weight of the dried tissue paper, an anti-viral lotion composition which is semisolid or solid at 20° C. and which comprises:

(A) from about 1 to about 25% of an organic acid capable of killing such viruses as rhinovirus and influenza which come into contact with the anti-viral lotion, wherein said anti-viral organic acid is a solid at room temperature and comprises a member selected from the group consisting of citric acid, adipic acid, glutaric acid, succinic acid, and mixtures thereof;

(B) from about 5 to about 25% of a hydrophilic solvent capable of aiding in the dissolution of the organic acid, said solvent may either be liquid or solid at room temperature and comprises a member selected from the group consisting of glycerin, propylene glycol, hexylene glycol, and polyethylene glycols ranging in molecular weight from about 200 to about 900, and mixtures thereof;

(C) from about 5 to about 60% of a substantially water free skin emollient having a plastic or fluid consistency at 20° C. and comprises a member selected from the group consisting of petroleum-based emollients, fatty acid ester emollients, fatty alcohol emollients, and mixtures thereof;

(D) from about 5 to about 50% of an agent capable of immobilizing said emollient on the surface of the tissue paper, said immobilizing agent having a melting point of at least about 35° C. and comprising a member selected from the group consisting of $C_{12}$–$C_{22}$ fatty alcohols, $C_{12}$–$C_{22}$ fatty acids, sorbitan stearates, waxes, and mixtures thereof;

(E) from 1% to about 50% of a non-ionic surfactant with said surfactant having an HLB value of at least about 4; and (F) optionally contains from about 0.1% to about 20% of a natural oil, vitamin, or other additive comprising a member selected from the group consisting of aloe, vitamin E, panthenol, camphor, thymol, menthol, eucalyptol, geraniol, lemon oil, methyl salicylate, clove and mixtures thereof.

2. The lotioned paper of claim 1 which has from about 5 to about 25% by weight of said lotion composition applied to at least one surface of the tissue paper.

3. The lotioned paper of claim 1 wherein said lotion composition comprises from about 5 to about 25% of said anti-viral organic acid.

4. The lotioned paper of claim 3 wherein said anti-viral organic acid is citric acid.

5. The lotioned paper of claim 3 wherein said anti-viral organic acid is a mixture of adipic acid, glutaric acid, and succinic acid.

6. The lotioned paper of claim 1 wherein said lotion composition comprises from about 5 to about 20% of a hydrophilic solvent selected from the group consisting of propylene glycol and polyethylene glycol having a molecular weight of from about 300 to about 500, and mixtures thereof.

7. The lotioned paper of claim 6 wherein said hydrophilic solvent is propylene glycol.

8. The lotioned paper of claim 1 wherein said emollient contains about 5% or less water and comprises a petroleum based emollient selected from the group consisting of mineral oil, petrolatum, and mixtures thereof.

9. The lotioned paper of claim 8 wherein said lotion composition comprises from about 10 to about 40% of the emollient consisting of petrolatum.

10. The lotioned paper of claim 1 wherein said immobilizing agent has a melting point of at least about 40° C.

11. The lotioned paper of claim 10 wherein said immobilizing agent comprises a $C_{14}$–$C_{22}$ fatty alcohol.

12. The lotioned paper of claim 11 wherein said immobilizing agent comprises a $C_{16}$–$C_{18}$ fatty alcohol.

13. The lotioned paper of claim 12 wherein said lotion composition comprises from about 10 to about 30% of an immobilizing agent comprising a mixture of cetyl and stearyl alcohols.

14. The lotioned paper of claim 1 wherein said non-ionic surfactant comprises an ethoxylated alcohol having an alkyl chain of from about 10 to about 22 carbon atoms and having an average degree of ethoxylation ranging from about 1 to about 30.

15. The lotioned paper of claim 14 wherein said ethoxylated alcohol has a alkyl chain length of from about 12 to about 22 carbon atoms and having an average degree of ethoxylation ranging from about 7 to about 13.

16. The lotioned paper of claim 15 wherein said non-ionic surfactant comprises from about 5 to about 25% of an ethoxylated alcohol having an alkyl chain length of from about 16 to about 18 carbon atoms and having an average degree of ethoxylation ranging from about 7 to about 13.

17. The lotioned paper of claim 16 wherein said non-ionic surfactant comprises from about 5 to about 25% of an ethoxylated alcohol consisting of a mixture of cetyl and stearyl alcohols ethoxylated to an average degree of ethoxylation of 10.

18. The lotioned paper of claim 8 wherein said hydrophilic solvent is selected from the group consisting of propylene glycol and polyethylene glycol having a molecular weight of from about 300 to about 500, and mixtures thereof.

19. The lotioned paper of claim 18 wherein said immobilizing agent comprises a $C_{16}$–$C_{18}$ fatty alcohol.

20. The lotioned paper of claim 1 wherein said lotion composition contains aloe, and vitamin E.

* * * * *